United States Patent [19]

Ishii et al.

[11] Patent Number: 6,043,061
[45] Date of Patent: Mar. 28, 2000

[54] PROCESS FOR PRODUCING AMIDE COMPOUND

[75] Inventors: Katsuo Ishii; Kouzo Murao, both of Kanagawa, Japan

[73] Assignee: Mitsubishi Rayon Co., Ltd., Tokyo, Japan

[21] Appl. No.: 09/176,802

[22] Filed: Oct. 22, 1998

[30] Foreign Application Priority Data

Oct. 23, 1997 [JP] Japan .................................. 9-308077

[51] Int. Cl.$^7$ .............................. C12P 13/02; C12N 9/78; C12N 9/88
[52] U.S. Cl. .......................... 435/129; 435/227; 435/232; 435/800; 435/803
[58] Field of Search .................................... 435/129, 800, 435/232, 227, 803

[56] References Cited

U.S. PATENT DOCUMENTS

| 2,481,580 | 9/1949 | Dreyfus | 260/465.8 |
| 5,519,162 | 5/1996 | Agarwal et al. | 560/248 |
| 5,866,379 | 2/1999 | Burlingame et al. | 435/129 |

FOREIGN PATENT DOCUMENTS

| 46-41290 | 12/1971 | Japan . | |
| 7-228563 | 8/1995 | Japan | C07C 255/03 |

*Primary Examiner*—Herbert J. Lilling
*Attorney, Agent, or Firm*—Sughrue, Mion, Zinn Macpeak & Seas, PLLC

[57] ABSTRACT

A process for producing an amide compound is described, wherein from a nitrile compound, the corresponding amide compound is produced by the action of nitrile hydratase, characterized in that the hydrocyanic acid concentration in a composition containing the nitrile compound is reduced by a chemical process, and thereafter nitrile hydratase acts on the nitrile compound. According to the invention, the decrease of the activity of the enzyme nitrile hydratase can be effectively suppressed so that an amide compound can be effectively produced from a nitrile compound.

10 Claims, No Drawings

PROCESS FOR PRODUCING AMIDE COMPOUND

FIELD OF THE INVENTION

The present invention relates to a process for producing an amide compound from a nitrile compound by the action of nitrile hydratase, which is an enzyme derived from a microorganism.

An amide compound is used in various fields as an industrially important substance. For example, an acrylamide has been used in a flocculating agent for waste water treatment, a paper strength reinforcing agent, a petroleum recovering agent, etc., and methacrylamide has been used in a paint, an adhesive, etc.

BACKGROUND OF THE INVENTION

Conventionally, an amide compound has been industrially produced by hydrating the corresponding nitrile compound using a reduced state copper as a catalyst. Recently, however, instead of the copper catalyst, a method using a microorganism enzyme as a catalyst has been developed, and such method is partially practiced now.

In an enzyme method, reaction conditions are gentle, and substantially no by-products are produced. Thus, such method can be effected according to an extremely simple process. Therefore, the enzyme method is considered to be effective as an industrial production method. Heretofore, many microorganisms have been found, which have an ability of hydrolyzing a nitrile compound to form an amide compound.

As such microorganisms, for example, mention can be made of genus Bacillus, genus Bacteridium, genus Micrococcus and genus Brevibacterium (JP-B-62-21519, corresponding to U.S. Pat. No. 4,001,081) (the term "JP-B" as used herein means an "examined Japanese patent publication"); genus Corynebacterium and genus Nocardia (JP-B-56-17918, corresponding to U.S. Pat. No. 4,248,968); genus Pseudomonas (JP-B-59-37951, corresponding to U.S. Pat. No. 4,637,982); genus Rhodococcus and genus Microbacterium (JP-B-4-4873, corresponding to U.S. Pat. No. 5,179,014); species Rhodococcus rhodochrous (JP-B-6-55148, corresponding to U.S. Pat. No. 5,334,519); and genus Rhodococcus strain (JP-B-7-40948, corresponding to U.S. Pat. No. 5,200,331).

While, in order to improve enzymatic activity and to suppress the decrease of enzymatic activity (deactivation) during a reaction, conventionally, various investigations have been conducted, which are as follows: a method wherein a reaction is effected at a low temperature of freezing point to 15° C. (JP-B-56-38118, corresponding to U.S. Pat. No. 4,248,968), a method wherein a substrate having a low concentration is continuously fed through plural feed openings (JP-B-57-1234, corresponding to U.S. Pat. No. 4,248,968), a method wherein a microorganism or the treated product thereof is treated with an organic solvent (JP-A-5-308980) (the term "JP-A" as used herein means an "unexamined published Japanese patent application"), a method wherein a reaction is effected in the presence of a higher unsaturated fatty acid (JP-A-7-265090), a method wherein a microorganism cell is treated by crosslinking with, for example, glutaric aldehyde (JP-A-7-265091 and 8-154691), etc.

Under the above-described circumstances, the present inventors have conducted various investigations regarding the improvement of the production of an amide compound according to an enzymatic method. As the result, it was found that deactivation with time during a reaction, which could not be overcome by a conventional method, was caused. It is natural that the greater this deactivation is, the more an enzyme is required for the reaction. Accordingly, the settlement of this problem is extremely important, especially, in industrial-scale production.

SUMMARY OF THE INVENTION

The present inventors have conducted extensive study and research efforts in order to solve the above-described problem. As the result, it could be found that a trace amount of hydrocyanic acid included in a composition containing a nitrile compound accelerated the deactivation of the enzyme nitrile hydratase. Further, it could be also found that by utilizing such composition comprising a reduced amount of hydrocyanic acid, the deactivation of the enzyme was lowered so that an amide compound could be efficiently produced from the nitrile compound, that is, by utilizing a smaller amount of the enzyme, a larger amount of an amide compound could be produced. Thus, the present invention was achieved.

That is, in accordance with the present invention, there is provided a process for producing an amide compound wherein from a nitrile compound, the corresponding amide compound is produced by the action of nitrile hydratase, characterized in that the hydrocyanic acid concentration in a composition containing the nitrile compound is reduced by a chemical process, and thereafter nitrile hydratase acts on the nitrile compound.

A nitrile compound, for example, acrylonitrile, is industrially produced by ammoxydation of propylene. Hydrocyanic acid is eliminated together with other by-products by distillation purification after the completion of the reaction. However, hydrocyanic acid which cannot be eliminated by this procedure is generally included in an amount of 0.1 to 5 ppm in a commercial product. Hydrocyanic acid generated by the subsequent decomposition of cyanhydrin remaining in a product is considered to be also included in the commercial product. The influence of such trace amount of hydrocyanic acid on deactivation could have never been expected heretofore.

DETAILED DESCRIPTION OF THE INVENTION

A nitrile compound used in the present invention (e.g., acrylonitrile) is not particularly limited as long as it is converted to a corresponding amide compound by the function of nitrile hydratase and is the main component in a composition which also comprises hydrocyanic acid in a concentration that causes enzyme deactivation. The amount of nitrile compound in the composition is about 90% or more. Examples of the nitrile compound include aliphatic saturated nitrites such as acetonitrile, propionitrile, succinonitrile and adiponitrile; aliphatic unsaturated nitrites such as acrylonitrile and methacrylonitrile; aromatic nitrites such as benzonitrile, phthalodinitrile; and heterocyclic nitrites such as nicotinonitrile. Typical examples thereof include nitrile compounds having 2 to 4 carbon atoms such as acetonitrile, propionitrile, acrylonitrile, methacrylonitrile, n-butyronitrile and isobutyronitrile. Particularly, acrylonitrile is preferred.

Further reduction of hydrocyanic acid remaining in a composition containing a nitrile compound used in the present invention can be effected according to a chemical process. Various reduction methods can be used. However, desirable methods do not increase the amount of by-products or impurities which may cause denaturation of a nitrile compound or lower the quality of an amide compound to be produced. As such methods, the following methods can be mentioned: a method wherein hydrocyanic acid in a composition containing a nitrile compound is converted to a metal complex; a method using an ion exchange resin; and in a case where a nitrile compound is an unsaturated nitrile, a method wherein hydrocyanic acid is added to the nitrile compound under an alkaline condition.

The method of converting to a metal complex comprises adding a metal, e.g., vanadium, chromium, manganese, lead, copper, silver, zinc, cobalt or nickel, which is capable of forming a metal cyanide complex by reacting with hydrocyanic acid, as a metal salt such as a nitrate, chloride, sulfate or carboxylate to a nitrile compound, to convert hydrocyanic acid to a metal cyano complex (refer to JP-A-7-228563). Further, in place of a metal salt, a metal alkoxide can be used (refer to U.S. Pat. No. 5,519,162). The amount of metal added is preferably about 0.00001 to 0.01%, though it varies with the concentration of hydrocyanic acid in a composition containing a nitrile.

In this case, if an enzyme converting a nitrile compound to an amide compound is not affected by a metal ion or a metal cyano complex, a metal salt is not required to be eliminated. However, in view of removing a greater amount of hydrocyanic acid, the metal cyano complex is preferably eliminated with an adsorbent, etc.

The removal of the metal cyano complex can be effected with, for example, an adsorbent (for example, an activated carbon, active alumina, zeolite, or silicagel) or an anion exchange resin.

The method using an ion exchange resin comprises contacting a nitrile compound with an anion exchange resin to eliminate hydrocyanic acid in the nitrile compound. As an anion exchange resin to be used, one having a highly porous (micro reticular) and a porous gel type anion exchange resin (for example, Amberlyst A-21 (manufactured by Japan Organo Co., Ltd.), Diaion WA 20, 21, 30 (for example, manufactured by Mitsubishi Chemical Co., etc.) are preferable, because they can exhibit sufficient ion exchange ability in a nitrile compound.

The ion exchange resin method may be carried out in a fixed bed, a movable bed or a fluidized bed, and it also may be either a batch method or a continuous method. Of these, the continuous fixed bed processing is preferred from the viewpoint of costs and workability. In this case, the passing rate of nitrile solution through the ion exchange resin is preferably about not more than 100 times the volume of the resin charged per 1 hour, though it varies with the concentration of hydrocyanic acid in a composition containing a nitrile.

However, such method using an anion exchange resin for the removal is readily accompanied by denaturation of a nitrile compound. Thus, sufficient investigation is required, for example, in regard to contacting time, contacting method, etc.

As the method wherein hydrocyanic acid is added to an unsaturated nitrile compound to form the saturated dinitrile compound under the alkaline condition, a method can be used wherein an aqueous solution is added to the nitrile (refer to U.S. Pat. No. 2,481,580) and a method can be used wherein nitrile is contacted with an anion exchange resin as an alkaline catalyst (JP-B-46-41290).

The aqueous alkaline solution for use in the present invention is not particularly limited, but should be selected among the alkaline which do not effect the quality of the amide and the activity of the enzyme. Examples of suitable aqueous alkaline solution are an aqueous solution of alkaline metal hdroxide and alkaline earth metal hydroxide and ammonia or amines, Of these, the aqueous solution of alkaline metal hydroxide and alkaline earth metal hydroxide and ammonia is preferred, an aqueous solution of sodium hydroxide and potassium hydroxide is particularly preferred.

The concentration of aqueous alkaline solution for use in the present invention is not particularly limited, but should be selected the range which do not effect the quality of amide and the activity of the enzyme. 0.00001 to 5 N of aqueous alkaline solution is preferred, particularly 0.00001 to 0.5 N of aqueous alkaline solution is preferred. The amount of aqueous alkaline solution for use in the present invention is not particularly limited. About 0.0001 to 10% by weight is suitable.

It is desirable to eliminate a larger amount of hydrocyanic acid. Usually, hydrocyanic acid is reduced to such an amount that the concentration of hydrocyanic acid in a nitrile compound is 3 ppm or less, preferably 1 ppm or less, and more preferably 0.5 ppm or less.

The nitrile hydratase is a metal enzyme wherein the active center thereof is constructed by iron, cobalt or the like. The enzyme deactivation is guessed to be caused by the coordination of iron or cobalt in the active center with cyanide. Accordingly, the nitrile hydratase in the present invention can be derived from any genus of microorganism.

The microorganisms capable of producing nitrile hydratase are as described above. Nitrile hydratase produced by these microorganisms can be all applied to the present invention. Among these, microorganisms belonging to genus Corynebacterium, genus Pseudomonas, genus Rhodococcus, genus Nocardia, genus Gordona, in particular genus Rhodococcus, which have a high enzymatic activity, are preferable. Recently, investigations have been conducted, wherein nitrile hydratase enzyme derived from these microorganisms is artificially modified, and nitrile hydratase is produced using other microorganisms. A microorganism which is made to develop nitrile hydratase activity according to a gene rearrangement technique also can be used.

As described in each of the above-mentioned publications, the interaction of nitrile hydratase with a nitrile compound is conducted by contacting the nitrile compound with the microorganism cell obtained by a culture or with the treated product thereof in an aqueous medium. The microorganism cell treated product is a ruptured microorganism cell, microorganism cell extract, or raw or purified enzyme extracted from a microorganism cell, and these microorganism cells and enzymes are with polyacrylamide, alginic acid, carrageenan, etc.

The present invention will now be illustrated in greater detail with reference to the following Examples. However, it is not intended that the present invention be limited to these Examples. Unless otherwise indicated, all percents in the following Examples and Comparative Examples are given by weight.

EXAMPLE 1 AND COMPARATIVE EXAMPLE 1

(1) Preparation of Microorganism Cell

Rhodococcus rhodochrous J-1 (FERM BP-1478) (JP-B-6-55148) having nitrile hydratase activity was aerobically cultured in a culture medium (pH 7.0) comprising glucose 2%, urea 1%, peptone 0.5%, yeast extract 0.3% and cobalt chloride 0.05%. The resulting cultured product was washed with 50 mM phosphate buffer (pH 7.0) to obtain a microorganism cell suspension (20% in terms of dried cell). To 500 g of the suspension was added 500 g of a mixed monomer solution comprising 20% of acrylamide, 2% of methylenebis acrylamide and 2% of 2-dimethylamino propylmethacrylamide, then the resulting mixture was sufficiently suspended. Successively, 2 g of 5% of ammonium persulfate and 2 g of 50% of tetramethyl ethylenediamine were added thereto to cause polymerization and gelation. The resulting gel was cut to 1 mm$^3$, which was washed with one liter of 0.5% sodium sulfate five times. Thus, immobilized microorganism cell particles, i.e., an acrylamide production catalyst, were obtained.

(2) Hydrocyanic Acid Reduction Treatment

To ten liters of acrylonitrile for industrial use (including 5 ppm of hydrocyanic acid) was added 100 g of 0.1 N sodium hydroxide, the resulting mixture was sufficiently stirred and dissolved, and then the resulting solution was allowed to stand for 30 minutes (alkali treatment). Thereafter, 20 g of acrylic acid aqueous solution at a concentration of 1 mol/liter was added thereto to cause neutralization. By this treatment, the hydrocyanic acid concentration in the acrylonitrile composition was decreased to 1.0 ppm.

(3) Amide Formation Reaction

To a separable flask having an internal volume of 5 liters was added 3200 g of sodium acrylate aqueous solution at a concentration of 0.2 g/liter. Then 3 g of the above-described immobilized microorganism cell was added thereto, which was stirred while controlling pH at 7.0 and temperature at 10° C.

Then acrylonitrile was continuously fed thereto so that the acrylonitrile concentration was constantly 2% and an accumulation reaction was continued until the acrylamide concentration reached 48%.

For comparison, an accumulation reaction was similarly continued until the acrylamide concentration reached 48% using an acrylonitrile which had not been subjected to the alkali treatment.

As a result, while the initial reaction rates were the same in both cases, in acrylonitrile which had been subjected to the alkali treatment, the deactivation was suppressed and it only took about half the amount of time to produce the acrylamide compared with the case using the acrylonitrile which had not been subjected to the alkali treatment.

The results are shown in Table 1.

TABLE 1

| Run No. | Alkali Treatment | Hydrocyanic Acid Concentration in Acrylonitrile | Reaction Time |
|---|---|---|---|
| Example 1 | + | 1.0 ppm | 120 hours |
| Comparative Example 1 | − | 5.0 ppm | 220 hours |

EXAMPLES 2 to 4 AND COMPARATIVE EXAMPLE 2

To 200 g of 50% acrylamide aqueous solution was added 0.1 g of the immobilized microorganism cell prepared in Example 1, followed by stirring at 15° C. To the same acrylonitrile for industrial use as that of Example 1 was added the metal salt shown in Table 2 for eliminating hydrocyanic acid so that the concentration of the metal was 10 ppm therein, and then the formed metal cyano complex was removed therefrom with active alumina. Each of the resulting acrylonitrile was added to the acrylamide solution obtained above in the amount of 4 g. 60 hours after starting the reaction, the acrylonitrile concentration was determined.

For comparison, the same treatment was applied to an acrylonitrile having no metal salts added thereto.

As a result, the initial reaction rates were the same. However, in acrylonitrile to which the metal salt had not been added, a lowering of the rate at which the amount of acrylonitrile decreased was observed, owing to the deactivation of the enzyme.

The results are shown in Table 2.

TABLE 2

| Run No. | Metal salt | Hydrocyanic Acid Concentration in Acrylonitrile (ppm) | Acrylonitrile Concentration (after 60 hrs) (%) |
|---|---|---|---|
| Example 2 | zinc chloride | 1.0 | 0.03 |
| Example 3 | nickel chloride | 0.7 | 0.02 |
| Example 4 | cobalt acetate | 1.9 | 0.2 |
| Comparative Example 2 | — | 3.1 | 0.7 |

EXAMPLES 5 to 7 AND COMPARATIVE EXAMPLE 3

(1) Hydrocyanic Acid Reduction Treatment

The same acrylonitrile for industrial use as that of Example 1 was placed into three plastic containers in an amount of 5 liters per each. Then, 50 ml of 0.1 N sodium hydroxide aqueous solution was added to each container and mixed sufficiently. Two minutes after the addition of sodium hydroxide, 1 mol/liter of acrylic acid aqueous solution was added to one container, ten minutes after the addition, 1 mol/liter of acrylic acid aqueous solution was added to another container, and twenty minutes after the addition, 1 mol/liter of acrylic acid aqueous solution was added to the other flask. Each amount of the 1 mol/liter acrylic acid solution added was 5 ml. Thus, all were neutralized.

(2) Amide Formation Reaction

The above-described acrylonitrile and water were continuously added to a 1 liter separable flask comprising 10 g of the immobilized microorganism cell prepared in Example 1 while controlling pH at 8 and the temperature at 20° C. The above-described acrylonitrile and distilled water were fed in order to control the acrylamide concentration at 50% and the acrylnitrile concentration at 2%. The reaction rate was found from the consumption rate of the acrylonitrile and the deactivation rate was found from the change of the reaction rate. On the basis of these values, the acrylamide productivity was calculated.

For comparison, the same process was also applied to acrylonitrile which had not been subjected to an alkali treatment.

As a result, the lower the hydrocyanic acid concentration in the acrylonitrile was, the lower the deactivation rate was. The acrylamide productivity per 1 g of the microorganism cell using the treated acrylonitrile was as high as twice that of the unreacted acrylonitrile.

The results are shown in Table 3.

TABLE 3

| Run No. | Alkali Treatment (min.) | Hydrocyanic Concentration in Acrylonitrile (ppm) | Acrylamide Productivity per Microbial Cell (g/g) |
|---|---|---|---|
| Example 5 | 2 | 3 | 1200 |
| Example 6 | 10 | 1 | 1800 |
| Example 7 | 20 | 0.5 | 2000 |
| Comparative Example 3 | — | 5 | 1000 |

According to the present invention, the decrease of the activity of the enzyme nitrile hydratase can be effectively suppressed so that an amide compound can be effectively produced from a nitrile compound.

While the invention has been described in detail and with reference to specific embodiments thereof, it will be apparent to one skilled in the art that various changes and modifications can be made therein without departing from the spirit and scope thereof.

What is claimed is:

1. A process for producing an amide compound from a nitrile compound by action of nitrile hydratase, which comprises reducing hydrocyanic acid concentration in a composition containing a nitrile compound by a chemical process, and then acting on said nitrile compound with nitrile hydratase, wherein the hydrocyanic acid concentration in the composition containing the nitrile compound is reduced to 3 ppm or less.

2. A process for producing an amide compound as claimed in claim 1, wherein the chemical process is a process of converting hydrocyanic acid to a metal complex.

3. A process for producing an amide compound as claimed in claim 1, wherein the hydrocyanic acid concentration is reduced to 1 ppm or less.

4. A process for producing an amide compound as claimed in claim 3, wherein the hydrocyanic acid concentration is reduced to 0.5 ppm or less.

5. A process for producing an amide compound as claimed in claim 1, wherein the nitrile compound is acrylonitrile.

6. A process for producing an amide compound as claimed in claim 1, wherein the chemical process is a process of converting hydrocyanic acid and an unsaturated nitrile compound to a saturated dinitrile compound under a alkaline condition.

7. A process for producing an amide compound as claimed in claim 6, wherein the unsaturated nitrile compound is acrylonitrile.

8. A process for producing an amide compound as claimed in claim 2, wherein the nitrile compound is acrylonitrile.

9. A process for producing an amide compound as claimed in claim 1, wherein the chemical process is a method using an ion exchange resin.

10. A process for producing an amide compound as claimed in claim 9, wherein the nitrile compound is acrylonitrile.

* * * * *